United States Patent [19]

Orlando

[11] Patent Number: 4,961,737
[45] Date of Patent: Oct. 9, 1990

[54] THERAPEUTIC DIAPER

[75] Inventor: Ramon A. Orlando, Vancouver, Canada

[73] Assignee: University of British Columbia, Vancouver, Canada

[21] Appl. No.: 264,236

[22] Filed: Oct. 28, 1988

Related U.S. Application Data

[63] Continuation-in-part of Ser. No. 203,537, May 23, 1988, abandoned, which is a continuation of Ser. No. 56,095, May 29, 1987, abandoned.

[30] Foreign Application Priority Data

Apr. 14, 1987 [CA] Canada .................................. 534715

[51] Int. Cl.$^5$ ............................................. A61F 13/16
[52] U.S. Cl. ............................... 604/385.2; 128/80 A; 128/87 C
[58] Field of Search .................. 604/385.1, 385.2, 391; 128/80 A, 87 C

[56] References Cited

U.S. PATENT DOCUMENTS

| 2,935,984 | 5/1960 | Kerr | 128/87 C |
| 3,618,608 | 11/1971 | Brink | 604/391 |
| 4,393,865 | 7/1983 | Lambert | 128/80 A |

FOREIGN PATENT DOCUMENTS 2335165  7/1977  France .................................. 604/391

Primary Examiner—John D. Yasko
Attorney, Agent, or Firm—Townsend and Townsend

[57] ABSTRACT

A diaper comprising an essentially rectangular panel of flexible material having an outer layer and an inner layer to define an internal pocket. Flexible arms extend outwardly from opposite longer sides of the panel adjacent a shorter edge, each of the arms having fasteners for releasably engaging a single corresponding fastener centrally located on the outer layer of the rectangular panel. Absorbent padding material is located in the internal pocket and is of an initial width and thickness to ensure that the wearer of the diaper is maintained in the lithotomy position or an approximation thereof by the absorbent padding bearing on the inner faces of the infant's thighs. Elastic strips are located parallel and adjacent the longer sides of the rectangular panel to seal the panel about the legs of the wearer and to prevent slippage of the diaper. The diaper is positioned on the wearer such that the essentially rectangular panel of flexible material extends from the wearer's waist, down under the crotch and back up to the waist with the inner layer lying against the skin. The flexible arms extends from the back of the wearer about the waist and diagonally downwardly for engagement with the single centrally located fastener at the front of the wearer.

2 Claims, 1 Drawing Sheet

THERAPEUTIC DIAPER

CROSS-REFERENCE TO RELATED APPLICATIONS

This application is a continuation-in-part of U.S. application Ser. No. 203,537 filed May 23, 1988, now abandoned which is a continuation of U.S. application Ser. No. b 056,095 filed May 29, 1987 now abandoned.

FIELD OF THE INVENTION

This invention relates to a diaper to reduce the incidence of congenital hip dislocation (CHD) in newborn children.

DESCRIPTION OF THE PRIOR ART

Congenital hip dislocation is a term that includes congenital hip dysplasia and congenital hip subluxation as well as dislocation. CHD can be treated in a new-born infant, by ensuring that the infant is kept in the lithotomy position or an approximation thereof. The lithotomy position is a position in which the legs are kept apart with the knees flexed and hips flexed and abducted. The fact that this position is of benefit to new-borns prone to CHD is demonstrated by studying the incidence of CHD in populations such as the Japanese. In Japan, until recently, infants were swaddled by binding the legs together with the hips and knees fully extended.

The Japanese reported a 6% incidence of CHD in their population and this was shown to be a direct result of the swaddling. By abolishing this practice and maintaining the new-born infant in the modified lithotomy position during the first four to six weeks of life the incidence of CHD dropped ten-fold to 0.6%. These results in Japan have been substantiated in large clinical trials reported in the medical literature of both Sweden and Yugoslavia.

A current method of treating CHD is to triple diaper any neonate with suspected CHD or variation of it in a process known as abduction diapering. This involves placing three consecutive diapers on the infant to introduce the desired flexion and abduction of the hips in conjunction with flexion of the knees. This procedure is carried out for the first four to six weeks of life in association with repeated hip examinations by an experienced orthopaedic surgeon through the first year of life. The latter is to pick up late diagnosis of CHD that may have been missed in early examinations.

The medical literature recommends that hip examinations be performed by one experienced examiner at each major maternity centre and demonstrates that multiple examiners increase the incidence of missed diagnoses. This incidence is even higher in hospitals distant from major teaching centres. Because of these factors, some countries, particularly Yugoslavia and Japan, employ the preventative practice of abduction diapering all infants. This has provided excellent results. Sweden employs regional experts to examine all new-borns and this technique has a slightly lower success rate. There are regional centres in North America where expert examinations are the norm, but these cover major teaching centres and leave the majority of new-borns in less experienced hands. Ideally, all new-borns should wear modified diapers for the first four to six weeks followed by regular hip examinations for the first year of life. The experience of the examiner will be less crucial as the abduction diapering technique will decrease the incidence of CHD even with no examinations.

U.S. Pat. No. 4,425,127 to Suzuki et al. and U.S. Pat. No. 4,397,645 to Buell teach examples of prior art disposable diapers that can be used in the abduction diapering technique. Unfortunately, the abduction diapering technique has disadvantages. First, the method is expensive and wasteful of materials as three diapers are used instead of one. Secondly, today's diapers were not designed to be worn over other diapers and often the outer diaper tends to come undone. Thirdly, the method requires additional time and effort on the part of the people doing the diapering. Some parents are not willing to expend the extra energy.

To overcome these problems, other prior art diapers have been developed specifically for reducing the incidence of congenital hip dislocation.

U.S. Pat. No. 2,935,984 to Kerr discloses a abduction splint for correcting hip dysplasia that uses a harness system to position an infant in the lithotomy position. The harness system does not provide a very comfortable arrangement for the infant.

U.S. Pat. No. 4,393,865 to Lambert discloses a diaper for infants intended to prevent or cure hip abnormalities such as dysplasia or subluxation. The diaper uses semi-rigid means mounted in the material of the diaper to orient an infant's thighs in a bent position approximately at ninety degrees with respect to the pelvis and in an abduction position at sixty degrees approximately. In Lambert's diaper, the semi-rigid means exerts pressure on the posterior aspect of the thighs in a sacro-ischial position as described by Lambert. This positioning of the semi-rigid means does not allow an infant to sleep in the preferred prone position (on the abdomen) without exerting undo pressure on the posterior of the thighs.

In a further embodiment Lambert teaches using a semirigid pad that bears against the lower side of the wearer's thighs. However, such a pad is prone to slippage or rotation from between the thighs of the infant rendering the pad less efficient in performing its abduction function. As well, Lambert's pad is made from polyurethane foam which is not particularly useful as an absorbing means for retaining fecal matter, and makes cleaning and drying of the diaper much harder.

In addition, Lambert uses fastening means comprising arms that horizontally encircle the waist and are secured at the back of the infant. The horizontal arrangement of the fastening means does not prevent drooping of the diaper from the waist so that the semi-rigid or padding means of Lambert are not correctly positioned on the wearer.

Furthermore, securing the fastening means at the back of the infant makes changing the diaper and maintaining hip adduction very difficult. Lambert's fastening means must be loosened and the diaper removed while the infant is on its stomach. Subsequently, the infant must be turned over onto its back without the benefit of padding means to maintain the legs in the lithotomy position. In the treatment and prevention of CHD, it is essential to maintain hip adduction continually throughout the critical period from birth to four to six weeks, even at diaper change and during periods of sleep.

SUMMARY OF THE INVENTION

Accordingly, there exists a need for a diaper that is applicable as a single diaper and overcomes the disadvantages of the prior art as outlined above.

The diaper of the present invention comprises:

an essentially rectangular panel of flexible material having an outer layer and an inner layer to define an internal pocket;

fastening means comprising flexible arms extending outwardly from opposite longer sides of said panel adjacent a shorter edge, each of said arms having engagement means for releasably engaging a single corresponding engagement means centrally located on the outer layer of said rectangular panel;

combined padding and absorbent means located in said internal pocket, said combined means being of an initial width and thickness to ensure that the wearer of the diaper is maintained in the lithotomy position or an approximation thereof by said combined padding and absorbent means bearing on the inner faces of the infant's thighs;

elastic means located parallel and adjacent the longer sides of said rectangular panel to seal said panel about the legs of the wearer and to prevent slippage of said diaper;

said diaper being positioned on the wearer such that the essentially rectangular panel of flexible material extends from the wearer's waist, down under the crotch and back up to the waist with said inner layer lying against the skin, said flexible arms of said fastening means extending from the back of the wearer about the waist and diagonally downwardly for engagement with said single centrally located engagement means at the front of the wearer.

The diaper of the present invention has combined absorbing and padding means that bear against the inner faces of the wearer's thighs and prevents adduction of the knees by providing resistance just above the knees. Such an arrangement prevents the slippage problem found in Lambert's design and allow the infant to sleep comfortably in the mandatory and preferred prone sleeping position in which the infant lies on its stomach.

In addition, the diaper of the present invention uses fastening arms that secure to the front of the diaper making changing the diaper easier as the procedure can be performed with the infant on its back and still in the lithotomy position. The fastening arms of the present invention also run diagonally about the waist of the wearer to the front engagement means which ensure a tight but comfortable fit and eliminates the problem of diaper slippage which can occur with horizontally arranged fasteners.

BRIEF DESCRIPTION OF THE DRAWINGS

Aspects of the invention are illustrated, merely by way of example, in the accompanying drawings, in which.

DESCRIPTION OF THE PREFERRED EMBODIMENTS

Figure 1:
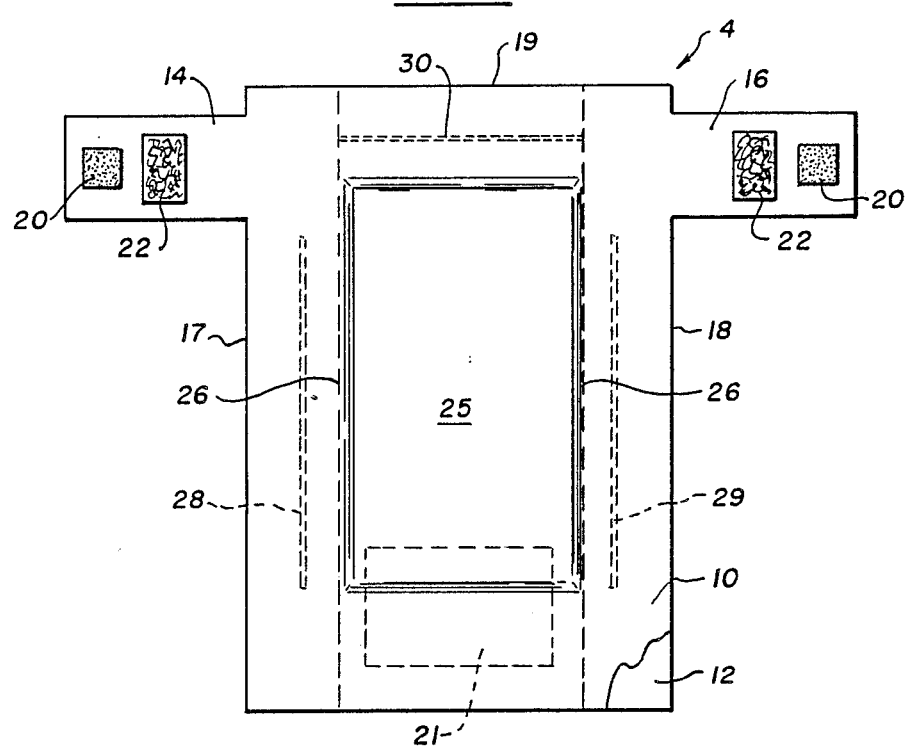
FIG. 1 is a plan view of a disposable diaper according to the present invention.

FIG. 1 shows a diaper according to the present invention. The diaper 4 comprises an essentially rectangular shape having an inner layer 10 and an outer layer 12, both of a soft, comfortable material such as cotton flannelette. Inner layer 10 contacts the skin of the wearer when the diaper is in place while outer layer 12 forms exterior of the diaper hence the names of the layers. Inner and outer layers 10 and 12 are joined to each other in a known manner such as stitching or gluing along all edges so that the two layers define a internal pocket between them.

Figure 2:
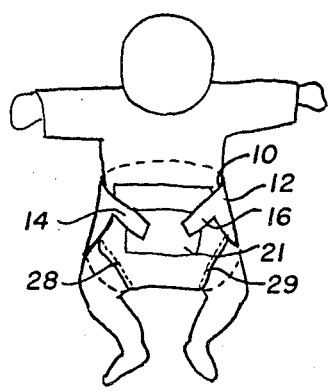
FIG. 2 shows the diaper of the present invention on an infant.

There are fastening means comprising two arms 14, 16 extending outwardly from the longer sides 17, 18 of the rectangular panel adjacent shorter edge 19. Arms 14 and 16 are flexible and made from the same cotton flannelette material as the rest of the diaper. The outer ends of both arms have attached engagement means 20. When the diaper of the present invention is positioned on an infant as shown in FIG. 2, the engagement means 20 of arms 14 and 16 are secured to a central corresponding engagement means 21 affixed to outer layer 12 at the front of the wearer. Preferably, engagement means 20 and 21 are corresponding pieces of conventional hook and loop fasteners with means 20 being the hook portion and central engagement means 21 being a loop portion. Hook and loop fasteners provide for quick and easy attachment of the diapers and permit easy and frequent adjustment and re-use without affecting gripping strength. Alternatively, re-fastenable tape, ties, buttons or other conventional engagement means can be used to attach the diaper about an infant.

If hook and loop fasteners are used, FIG. 1 shows how arms 14 and 16 may be provided with corresponding loop pads 22 directly beside each hook portion 20. These pads are useful during cleaning of the diapers. The arms are folded over on themselves to engage the hook and loop fasteners so that the hook fasteners 20 are not exposed to catch and snag with other clothing.

Combined padding and absorbent means 25 are provided within the internal pocket between inner layer 10 and outer layer 12. Preferably, combined padding and absorbent means 25 comprise a conventional absorbent padding material such as needle punch. Needle punch is a preferred material as it has good moisture absorbing capacity and is easy to wash requiring only a single drying cycle of a conventional washing machine to dry. The present invention therefore provides a diaper that can be reused any number of times after washing.

As shown in FIG. 1, padding and absorbent means 25 occupies the majority of the internal pocket between layers 10 and 12 but does not completely fill that space. The absorbent padding is located within the pocket by stitching 26 through layers 10 and 12 and needle punch 25 along the longer edges of the padding. Stitching 26 creates the only major seams found on inner layer 10. Otherwise, all other locating stitching extends through outer layer 12 and the needle punch to anchor the padding and absorbent means 25 to the outer layer. This arrangement minimizes the length of seams on the inner surface 10 so that there is less chance of irritating the infant's skin.

The diaper of the present invention is positioned on an infant as shown in FIG. 2. The infant is placed on the centre of inner layer 10 with the hips flexed and abducted such that the infant's legs extend over the longer side edges 17 and 18 of the rectangular panel. The diaper is then positioned on the infant such that the essentially rectangular panel of flexible material extends from the front of the infant's waist, down under the crotch and back up to the back of the waist with inner layer 10 lying against the skin to provide a comfortable surface. Flexible arms 14 and 16 are extended from the back of the infant about the waist and diagonally downward for engagement with the single central engagement means 21 positioned at the front of the infant. By orienting arms 14 and 16 in a diagonal direction, the diaper is prevented from sliding inferiorly from the infant's waist as occurs with the horizontally arranged attachment means of the prior art. Any slippage of the diaper is undesirable in the present invention and the prior art as it displaces the padding means thereby rendering the diaper useless in performing its function of maintaining the infant in the lithotomy position.

Combined padding and absorbent means 25 is wider across the shorter dimension of the diaper than in conventional diapers. This facilitates performance of the previously mentioned function of maintaining the wearer in the lithotomy position. The majority of today's conventional diapers have an effective crotch padding width of 12.7 cm. According to the present invention, padding and absorbent means 25 preferably comprises a 1.3 cm thickness of needle punch with a width across the shorter dimension of the diaper of 15.2 cm. The greater width of padding and absorbent means 25 causes abduction flexion of the hips with edges 17 and 18 of the diaper resting on the inner face of the infant's thighs just above the knees causing flexion of the knees. Abduction resistance is more suitably placed on the inner aspect of the thighs than on the lower or posterior aspect of the thighs as is done in the prior art. In the prior art, particulary U.S. Pat. No. 4,393,865 to Lambert, semi-rigid orientation means are shown that engage against the posterior aspect of the infant's thighs. Such an arrangement exerts pressure on the thighs when the infant sleeps in the prone position on the abdomen making it uncomfortable for the child. In contrast, the padding and absorbent means of the present invention are positioned to afford the infant the mandatory and preferred prone sleeping position without discomfort. It is fundamental to the design of a diaper for reducing the incidence of CHD that an infant wearing the diaper be able to sleep comfortably in the prone position.

Referring to FIG. 1, there are elastic strips 28, 29 provided between layers 10 and 12 adjacent the longer edges of the diaper. These elastic strips serve to seal the diaper about the legs of the wearer and also assist in locating the diaper on the wearer so that the diaper is not prone to slippage common in prior art diapers of this type. In addition, elastic strip 30 runs across the shorter edge of the diaper between arms 14 and 16. Elastic strip 30 acts to tension the flexible arms as they extend about the waist so that the diapers maintain a snug and comfortable fit on the infant.

The fact that flexible arms 14 and 16 attach to central engagement means 21 at the front of the diaper make changing the diaper and maintaining the lithotomy position of the infant very easy. In the treatment and prevention of CHD it is important that the infant be kept constantly in the lithotomy position during the critical period from birth to four to six weeks. By having the engagement means attach to the front of the diaper, the infant must be changed while on its back, its hips and legs falling naturally into the lithotomy position when the diaper is removed thereby assuring that the preferred position is not lost even during diaper changes.

The diaper of the present invention provides a comfortable, easily cleaned diaper capable of fitting all infants weighing from four pounds to twelve pounds, the weight extremes encountered throughout the period from birth to four to six weeks when wearing of the diaper is recommended. The present invention provides a diaper having combined padding and absorbent means to cause abduction and flexion of the hips and flexion of the knees of the wearer. Maintaining the wearer in this lithotomy position with the legs apart and the knees and hips sl ightly flexed for the first four to six weeks of life serves as a preventative measure to significantly lessen the incidence of CHD.

I claim:
1. A diaper comprising:
an essentially rectangular panel of flexible material having an outer layer and an inner layer to define an internal pocket;
fastening means comprising flexible arms extending outwardly from opposite longer sides of said panel adjacent a shorter edge, each of said arms having an engagement means comprising hook and loop fasteners for releasably engaging a single corresponding engagement means centrally located on the outer layer of said rectangular panel;
combined padding and absorbent means comprising needle punch located in said internal pocket by stitching to the outer layer of said rectangular panel such that the stitching does not come into contact with the wearer's skin, said combined means being of an initial width and thickness to ensure that the wearer of the diaper is maintained in the lithotomy position or an approximation thereof by said combined padding and absorbent means bearing on the inner faces of the infant's thighs;
elastic means located parallel and adjacent the longer sides of said rectangular panel to seal said panel about the legs of the wearer and to prevent slippage of said diaper;
elastic means extending parallel and adjacent said shorter edge between said outwardly extending arms of said fastening means;
said diaper being positioned on the wearer such that the essentially rectangular panel of flexible material extends from the wearer's waist, down under the crotch and back up to the waist with said inner layer lying against the skin, said flexible arms of said fastening means extending from the back of the wearer about the waist and diagonally downwardly for engagement with said single centrally located engagement means at the front of the wearer.
2. A diaper as claimed in claim 1 wherein the loop fasteners are disposed on said flexible arms and further comprising a loop portion positioned beside each hook fastener.

* * * * *